United States Patent [19]

Grasshoff et al.

[11] 3,932,480

[45] Jan. 13, 1976

[54] BENZYLTHIOSULFURIC ACID SALTS

[75] Inventors: J. Michael Grasshoff, Hudson; Lloyd D. Taylor, Lexington, both of Mass.

[73] Assignee: Polaroid Corporation, Cambridge, Mass.

[22] Filed: May 3, 1974

[21] Appl. No.: 466,630

Related U.S. Application Data

[60] Continuation-in-part of Ser. No. 230,064, Feb. 28, 1972, abandoned, which is a division of Ser. No. 99,310, Dec. 17, 1970, Pat. No. 3,698,898.

[52] U.S. Cl.................. 260/453 R; 96/3; 96/29; 96/66.3; 96/66.5; 96/76; 96/109; 96/111; 260/479 R
[51] Int. Cl.².................................. C07C 161/05
[58] Field of Search..................... 260/479 R, 453 R

[56] References Cited

OTHER PUBLICATIONS

Esayan et al., Chem. Abstracts, Vol. 65, (1966), p. 2162.
Abramyan, Chem. Abstracts, Vol. 70, (1969), Abstract No. 19052k.

*Primary Examiner*—James A. Patten
*Attorney, Agent, or Firm*—Mart C. Matthews; Philip G. Kiely

[57] ABSTRACT

Novel compounds are disclosed which release a silver halide solvent in the presence of alkali, which compounds may be defined as quinone-or naphthoquinone-methide precursors containing the silver halide solvent moiety. These novel compounds are useful in photographic products and processes.

4 Claims, No Drawings

BENZYLTHIOSULFURIC ACID SALTS

CROSS REFERENCE TO RELATED APPLICATIONS

This application is a continuation-in-part of our co-pending application Ser. No. 230,064, now abandoned, filed FEB. 28, 1972, which in turn was a divisional of application Ser. No. 99,310, filed Dec. 17, 1970 and now U.S. Pat. No. 3,698,898, issued Oct. 17, 1972.

BACKGROUND OF THE INVENTION

1. Field of the Invention

This invention relates to chemistry and, more specifically to novel compounds per se.

2. Description of the Prior Art

In various photographic systems for forming images, whether in black-and-white or in color, it is often desirable to include in the photographic film unit one or more of the various photographic reagents required for development and/or to enhance image quality. This practice extends to both conventional systems for forming negative images and to the various systems such as diffusion transfer, wherein a positive image in silver or in color is obtained.

In many instances, the photographic reagent may be contained initially in either the processing composition applied for development and image formation or in the film unit, the latter being preferred to reduce and hence simplify the number of ingredients required in the processing composition.

In other instances, the particular photographic reagent desired is not sufficiently stable in alkali to provide the requisite shelf life for the processing composition or the reagent is incompatible and/or reactable with another reagent of the composition and hence must be contained initially in the film unit.

In still other instances, the reagent must be provided at some particular time in the development process, which requires that it be contained in a specified layer or in specified proximity to another layer in the film unit.

In all of the foregoing instances it is desirable that the reagent be contained in the desired layer or layers of the particular film unit in such a manner that it is stable, non-migratory or non-diffusible, and yet available when required in the development process.

The present invention is directed to novel compounds which provide advantageous means for incorporating reagents of the above-mentioned type in the photographic product.

The art contains several references to "hydrolyzable" photographic reagent precursors such as, for example, reference in U.S. Pat. No. 3,265,498, issued Aug. 9, 1966 to hydrolyzable development restrainer precursors. However, prior to the present invention, the novel quinone and naphthoquinone-methide precursors of the present invention have been unknown in the art. Our U.S. Pat. No. 3,685,991, issued Aug. 22, 1972 describes integral photographic silver diffusion transfer products and processes employing novel compounds within the scope of this invention.

SUMMARY OF THE INVENTION

Novel compounds are provided in accordance with this invention which release a silver halide solvent in the presence of alkali. Since these compounds split off a quinone-methide or naphthoquinone-methide compound in alkali, they may be defined generically as quinonemethide or naphthoquinone-methide precursors containing a silver halide solvent moiety. They may also be defined as phenols or naphthols (including protected derivatives thereof) having a silver halide solvent moiety including a sulfur atom which is bonded to a nuclear carbon atom in a position ortho or para to the hydroxyl group through a methylene linkage.

The novel compounds of the invention are useful in photographic processes and products wherein it is desireable that a silver halide solvent be made initially unavailable for participation in the photographic process in a non-active, stable form, and yet is made available at some subsequent time in the process, e.g. when contacted by the aqueous alkaline developing medium.

Detailed Description of the Invention

The novel compounds of the present invention may be represented by the formula:

A.

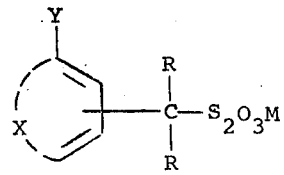

wherein:
X represents the atoms necessary to complete a benzene or naphthalene nucleus, including substituents thereon, if any, e.g. a "ballasting" or "hydrolysis-retarding" substituent;
Y is hydroxyl or protected hydroxyl, i.e. a substitutent which upon hydrolysis provides a hydroxyl radical, e.g. acyloxy such as acetoxy, carbethoxy, etc. M is an alkali metal, e.g., sodium or potassium; and each R represents hydrogen or a lower (1–4 carbon) alkyl group, e.g., methyl, ethyl, etc., with the -C-$S_2O_3$M linkage being bonded to a nuclear carbon atom of X in a position ortho or para to the Y substituent.

As indicated, X may include nuclear substituents if desired, for example, to accomplish a specified purpose. As an illustration, X may include an "anchoring" or "ballasting" substituent which renders the compound essentially nondiffusible, i.e. a substituent such as is described, for example, in U.S. Pat. No. 3,443,940, e.g., an alkyl group containing at least ten carbon atoms, such as decyl, dodecyl, stearyl, oleyl, etc., linked directly to the aromatic nucleus or indirectly through an appropriate linking group such as a -CONH-, alkylene-CONH- or

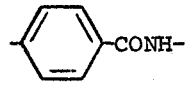

substituent; or an aromatic ring, e.g., of the benzene or naphthalene series, or a heterocyclic ring, which rings may be either bonded to a single carbon atom of the aromatic nucleus formed by the X atoms or fused thereto by being bonded to a pair of adjacent carbon atoms; or a polymeric substituent, e.g., a high polymer backbone; or a plurality of short chain radicals which together provide the anchoring moiety.

If desired, the benzene or naphthalene nucleus of the novel compounds of this invention may contain other substituents providing particular desired functions, e.g., a substituent which will retard or slow down the hydrolysis rate and hence control the rate or time of release of the photographic reagent, as will be described hereinafter.

Accordingly, X may comprise a group of the formula:

B. 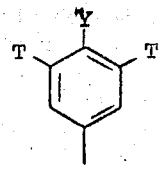

wherein T is hydrogen, alkyl, e.g. lower (1-4 carbon) alkyl such as methyl, propyl, t-butyl, etc., aryl, e.g. phenyl, or halide, e.g. chloro; or a group of the formula:

C. 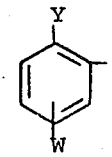

wherein W is hydrogen, alkyl, aryl, halide, nitro, alkoxy, amino, amidoalkyl, carbonyl, carboxyl, sulfo, formyl, etc.; or a group of the formula:

D. 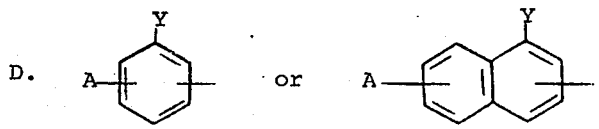

wherein A is hydrogen, or an anchoring or ballasting substituent as previously described, e.g. dodecylamidoalkyl or a high polymer backbone. Y in each instance has the definition given previously.

As examples of compounds within the scope of this invention, mention may be made of:

1. 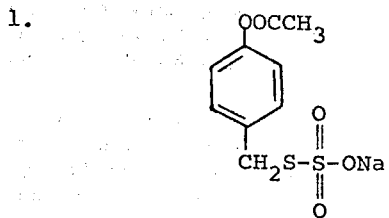

sodium S-(p-acetoxybenzyl)thiosulfate

2. 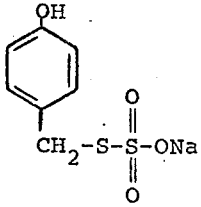

sodium S-(p-hydroxybenzyl)thiosulfate

3. 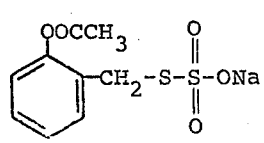

sodium S-(o-acetoxybenzyl)thiosulfate

4. 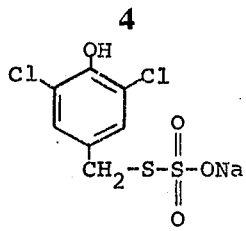

sodium 5-(4-hydroxy-3,5-dichlorobenzyl) thiosulfate

In general, the novel compounds of this invention are readily obtainable by appropriate known replacement or substitution reactions. In such reactions, it may be and usually is, desireable to protect the phenolic hydroxyl group during the reaction step by which the silver halide solvent moriety is incorporated.

The following example shows by way of illustration and not by way of limitation the preparation of the novel compounds of this invention.

EXAMPLE 1

9.92 g. of sodium thiosulfate ($Na_2S_2O_3 \cdot 5H_2O$) were dissolved in 20 ml. of water and the resulting solution was heated to 70°C while stirring. A solution of 7.38 g. of p-acetoxybenzyl chloride in 20 ml. of 2B ethanol was then added dropwise. The resulting clear solution was then gently refluxed for 40 minutes. After cooling, the solvent was evaporated using a thin film evaporator to yield a crystalline residue which was then extracted with about 150 ml. of boiling ethanol, followed by filtration. Refrigeration and filtration of the resulting precipitate yielded about 7 g. of sodium S-(p-acetoxybenzyl) thiosulfate, the compound of formula 1, white platelets, m.p. 220°C (decomp.), soluble in water, alkali, warm ethanol.

| Elemental Analysis: | C | H | Cl |
|---|---|---|---|
| Calculated: | 38.1 | 3.2 | 22.5 |
| Found: | 37.9 | 3.2 | 22.4 |

The S-(o-acetoxybenzyl) thiosulfate isomer of formula 3 may be prepared by substituting o-acetoxybenzyl chloride in the above example.

The novel compounds of the invention are useful in the field of photography, and particularly in photographic film units wherein it is desireable that a silver halide solvent be contained in a layer or layers thereof in such a manner that it is stable, non-migratory or nondiffusible, and yet can be made available when required in the photographic process. One such use is fully and adequately described in our aforementioned U.S. Pat. No. 3,685,991, issued Aug. 22, 1972, wherein compounds within the scope of this invention are employed in integral photographic silver diffusion transfer film units which comprise an additive multicolor screen, silver precipitating nuclei and a layer comprising photosensitive silver halide crystals. In said patent, which is herein incorporated by reference in its entirety, a quinone-or naphthoquinone-methide precursor of the present invention containing a silver halide solvent moiety is disposed in a layer of the film unit, preferably the layer containing the photosensitive silver halide, in this essentially inactive form, yet splits off the active silver halide solvent when contacted with the alkaline medium used to process the film unit. Employment in the film unit of a developing agent or precursor in association with a silver halide solvent precursor of the present invention is stated in said patent to permit processing of the exposed film unit to be accomplished with a minimum of externally applied processing reagent. For a more detailed description of this particular embodiment, reference should be made to the aforementioned incorporated patent.

It should be understood that the present compounds are not limited in their usefulness to any particular photographic system. In any of the known systems for forming positive and/or negative silver or dye images, it is commonly desireable to employ photographic reagents performing desired functions, e.g. silver halide solvents to complex silver halide and render it diffusible, etc., and the compounds of the present invention provide advantageous means for incorporating these reagents in the photographic product.

The following example shows by way of illustration and not by way of limitation the use of the novel compounds of this invention in photographic products and systems for preparing visible images.

EXAMPLE 2

On a gelatin subcoated triacetate film base was coated a layer containing a gelatino silver iodobromide emulsion at a coverage of 100 mgs./ft.$^2$ of silver, 40 mgs./ft.$^2$ of toluhydroquinone and 300 mgs./ft.$^2$ of the compound of formula 1, sodium S-(p-acetoxybenzyl) thiosulfate. The resulting film unit was exposed and then developed by applying between the thus exposed element and an image-receiving element form a Polaroid Type 107 Land film comprising a siliceous silver-receptive stratum containing silver precipitating nuclei, at a gap of 0.0030 inch, a developing composition containing the following proportions of ingredients:

| | |
|---|---|
| Water | 111.25 cc. |
| Sodium hydroxide | 6.25 g. |
| Sodium carboxymethyl cellulose | 6.0 g. |

After about 60 seconds the respective elements were separated to reveal a positive silver transfer image.

A film unit prepared in Example 2 was subjected to a standard aging test for five days at 120°F prior to use. Exposure and development in the foregoing manner produced a like positive silver image of substantially the same silver density, indicating no appreciable instability of the film unit under the test conditions. In contrast with the foregoing results, attempts to include a water-soluble silver halide solvent, e.g., sodium thiosulfate, in the silver halide layer produced no silver image.

Since certain changes may be made in the above products and processes without departing from the scope of the invention herein involved, it is intended that all matter contained in the above description shall be interpreted as illustrative only and not in a limiting sense.

What is claimed is:
1. A compound having the formula:

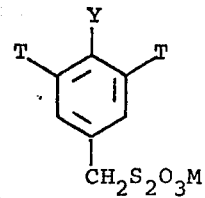

or

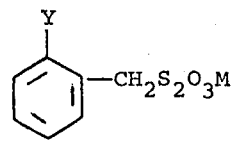

wherein Y is hydroxyl or acetoxy; both T's are the same and represent hydrogen, chloro, or lower alkyl; and M is sodium or potassium.

2. Sodium S-(p-acetoxybenzyl) thiosulfate.
3. Sodium S-(p-hydroxybenzyl) thiosulfate.
4. Sodium S-(o-acetoxybenzyl) thiosulfate.

* * * * *